US00PP26357P2

(12) United States Plant Patent
Hansen

(10) Patent No.: US PP26,357 P2
(45) Date of Patent: Jan. 26, 2016

(54) *HEUCHERA* PLANT NAMED 'BERRY TIMELESS'

(50) Latin Name: ***Heuchera* hybrid**
Varietal Denomination: Berry Timeless

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 135 days.

(21) Appl. No.: 13/999,518

(22) Filed: Mar. 6, 2014

(51) Int. Cl.
*A01H 5/02* (2006.01)

(52) U.S. Cl.
USPC ..... Plt./440

(58) Field of Classification Search
USPC ..... Plt./440
See application file for complete search history.

(56) References Cited

U.S. PATENT DOCUMENTS

PP24,563 P3 * 6/2014 Egger ..... Plt./440

* cited by examiner

*Primary Examiner* — June Hwu

(57) ABSTRACT

The new and distinct hybrid plant of *Heuchera* named 'Berry Timeless' with foliage having broad silver variegation and dark-green regions surrounding the veins, flowering without vernalization requirement, from early summer to fall frost with coloring of light pink petals and effective, persistent, dark-rose calyxes just above foliage suitable for landscaping or as cut flower or foliage decoration. The new plant is vigorous, compact in habit and tolerates heat and humidity well.

1 Drawing Sheet

Botanical denomination: *Heuchera* hybrid.
Cultivar designation: 'Berry Timeless'.

BACKGROUND OF THE INVENTION

The present invention relates to a new and distinct cultivar of Coral Bells in the Saxifragaceae family and given the cultivar name of 'Berry Timeless'. *Heuchera* 'Berry Timeless' was hybridized by Hans A. Hansen on Jan. 24, 2012 at a nursery in Zeeland, Mich., USA and originally given the breeder code of H12-129-01. The seed or female parent was a selected, unreleased, proprietary seedling known as *Heuchera* K10-46-01 (not patented) and the pollen or male parent was *Heuchera* 'Cherry Cola' U.S. Plant Pat. No. 22,967. The new invention has a mixture of *Heuchera americana, H. brizoides, H. micrantha* and *H. villosa* in the pedigree.

*Heuchera* 'Berry Timeless' was first selected in the spring of 2012 and passed final evaluation in the fall of 2013 from among thousands of other seedlings from the same cross and hundreds of other crosses. *Heuchera* 'Berry Timeless' was has been asexually propagated by division at the same nursery in Zeeland, Mich. and by careful tissue culture propagation, and the resultant plants have remained stable and exhibit the same characteristics as the original plant for multiple generations.

*Heuchera* 'Berry Timeless' has not been made publically available or sold anywhere in the world prior to the filing of this application. Any public disclosure of 'Berry Timeless' has been by the inventor, or one who obtained the material either directly or indirectly from the inventor, and any such disclosure has not been made more than one year prior to the application of this invention.

BRIEF SUMMARY OF THE INVENTION

In comparison to the female parent, K10-46-01, the new plant has flowers that are clear pink rather than more coral, and foliage of the new plant is more silver. In comparison to the male parent, 'Cherry Cola', the new plant has foliage that is more dark green and broad silver variegation rather than brassy-reddish foliage with muted variegation of 'Cherry Cola'. The flowers of 'Cherry Cola' are also deeper red compared to the clear light pink flowers of 'Berry Timeless. 'Berry Timeless' also flowers for a much profusely and for a longer period than either parent.

The nearest comparison varieties are *Heuchera* 'Venus' (not patented), *Heuchera* 'Peppermint' U.S. Plant Pat. No. 24,563 and *Heuchera* 'Paris' U.S. Plant Pat. No. 18,881. Both 'Venus' and 'Peppermint' have similar silver and dark green foliage, but the foliage of 'Berry Timeless' has more acute leaf lobe apexes. The flowers are more free-flowering than either of the parents or the comparison plants. The flowers on 'Paris' are more spread out and more red than the clear pink of 'Berry Timeless'.

*Heuchera* 'Berry Timeless' differs from its parents as well as all other Coral Bells known to the applicant in the following combined traits:

1. The foliage color of 'Berry Timeless' is a dark green with broad silver variegation almost to the point of just dark green veins.
2. Flowers are profuse over a long period of time on densely branched panicles with first flowers coming just above foliage.
3. Flowers without the requirement of a vernalization period and with frequent repeat flowering.
4. Flower petal color is clear light pink with persistent rose-colored calyxes.
5. The new plant is vigorous, compact in habit and tolerates heat and humidity.

BRIEF DESCRIPTION OF THE DRAWINGS

The photographs of the new plant demonstrate the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
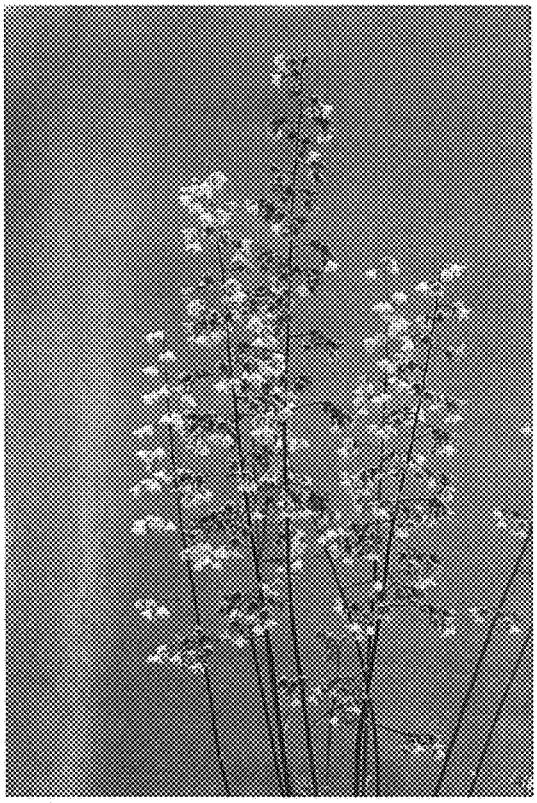
FIG. 1 shows a close-up of the flower scape.
Figure 2:
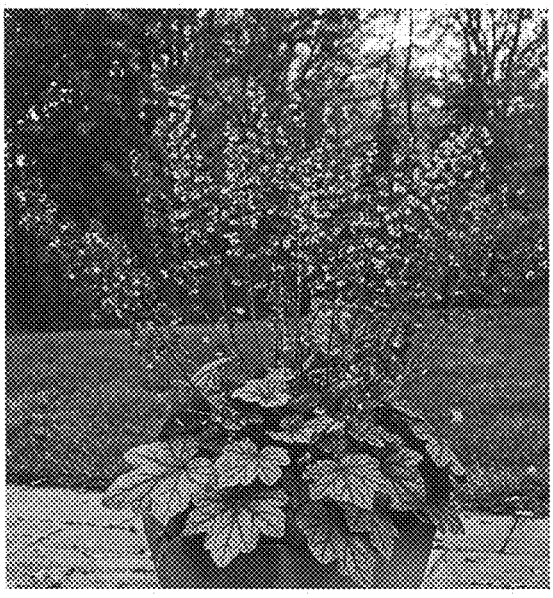
FIG. 2 shows the whole plant in flower with dark green and silver foliage.

The following description is based on a two-year old plant growing in a lightly shaded greenhouse in Zeeland, Mich., USA. The new plant has not been grown under all possible environments, and asexually propagated plants may phenotypically appear different under different conditions such as light, temperatures, fertilizer, and water, without any difference in genotype.

The color descriptions used are from the 2001 edition of The Royal Horticultural Society Colour Chart except where common dictionary terms are used.

Parentage:

*Female* (*seed parent*).—Proprietary unreleased *Heuchera* seedling K10-46-01 (not patented).

*Male* (*pollen*).—'Cherry Cola' U.S. Plant Pat. No. 22,967.

Plant habit: Hardy herbaceous perennial with multiple branched basal stems each with a basal rosette of foliage; radially-symmetrical mounded foliage about 16 cm tall and 35 cm in diameter.

Roots: Fibrous, finely branched; color variable with soil make up, usually near white, nearest RHS 155D.

Growth rate: Rapid, rooting from cutting in two weeks and finishing in three-liter container in about 3 months.

Foliage: Cordate, sparsely hirsutulous below and glabrous above, palmately lobed with up to seven main lobes each having three or more sub-lobes; blade up to about 11.0 cm long and 10.0 cm wide, average about 10.5 cm long and 10.0 cm wide; apex broadly acute with lateral lobes broadly acute; lobes dissected or indented by up to 1.5 cm; apical lobe largest at about 5.0 cm across at base and lateral lobes decreasing in size going toward base from 3.3 cm across to 2.0 cm; mostly flat surfaced with slightly impressed adaxial veins; base distinctly cordate extending backward about 2.5 cm from petiole; margin hirsutulous with lobules finely fimbriate to mucronate at apices; serrate, especially when young, becoming more crenulate with maturity; undulation of leaf blade margin absent; leaf blade rugosity absent; abaxial and adaxial surfaces matte, glossiness absent;

Leaf color:

*Young emerging leaves adaxial surface*.—Nearest RHS 136A surrounding main and secondary veins to 1.0 to 1.5 mm on either side, closer to RHS 147D than RHS 147C between the veins.

*Young emerging abaxial surface*.—Between RHS 147C and RHS 148C between the veins with shadows of between RHS 147B and RHS 147A on 1.0 to 1.5 mm on either side of the main and secondary veins.

*Mid-season flowering time leaves adaxial surface*.—Dark green surrounding veins between RHS N189A and RHS 139A to 1.0 to 2.0 mm on either side of the main and secondary veins, surface flanked by the veins between RHS 191C and RHS 191D.

*Mid-season flowering time abaxial leaf surface*.—Nearest RHS 148C throughout surface; fall and winter foliage becoming tinted to marbled with between RHS 182A and RHS 182B adaxial and between RHS 185B and RHS 185C abaxial.

Leaf margin: Serrate, especially when young, becoming more crenulate with maturity; hirsutulous with lobules finely fimbriate to mucronate at apices.

Leaf apex: Broadly acute, mucronate.

Leaf base: Cordate, auriculate with slightly overlapping lobes.

Leaf surface: Sparsely hirsutulous abaxial and glabrous adaxial; adaxial slightly vernicose; abaxial matte surface.

Leaf quantity: Dense, about 50 per plant.

Veins: Palmate, hirsutulous and ridged abaxial, glabrous and impressed adaxial.

Vein color: On emerging foliage adaxial main and secondary veins nearest RHS 145A, minor veins same color as surrounding tissue; emerging foliage abaxial main and secondary veins nearest RHS 145A with minor veins between RHS 146A and RHS 146B; mid-season flowering time adaxial main, secondary and some minor veins nearest RHS 145A with very small veins same as the surrounding tissue; mid-season flowering time abaxial main and secondary veins nearest RHS 145A with minor veins between RHS 146A and RHS 146B.

Petiole: Cylindrical, hirsutulous; about 11.0 cm long and 2.5 mm wide.

Petiole color: Ranging from nearest RHS 144A.

Inflorescence: Hirsutulous, cylindrical; nearly-vertical branched panicle, with slight bend at branch nodes; about 10 panicles per plant; flowering portion about 30 cm tall and 7.0 cm diameter just above foliage; remain effective for nearly three months.

Panicle branches: Beginning about 12.0 cm above soil, 20 to 25 branches per panicle; lower branches at about 60 degrees from horizontal and upper branches closer to 90 degrees from vertical or horizontal; lower branches about 4.5 cm long and decreasing distally, about 0.5 mm diameter; panicle head about 9 cm across and 38 cm tall; about 3 to 12 flowers per branch, average about 6.3 flower per branch and average of about 140 flowers per panicle.

Peduncle: Stiff, cylindrical, densely hirsutulous, about 45 cm long and 3.5 mm diameter at base; semi-upright curving to about 75 degrees from horizontal.

Peduncle color: Between RHS 146A and RHS 146B with tinting increasing distally to become nearest RHS 183A.

Pedicel: Cylindrical, hirsutulous, 3.0 to 4.0 mm long and about 0.5 mm diameter.

Pedicel color: Between RHS 187B and RHS 187C proximally and distally nearest RHS 186A.

Bracts: At panicle main nodes incised to five lobed, about 12 mm long and 3.0 mm wide decreasing distally, with acute apices and lobes, base sessile and truncate.

Bract color: Nearest RHS 146A with base tinted with RHS N186D.

Flower buds one day prior to opening: Ellipsoid, with rounded base and apex; about 3.0 mm long and 2.0 mm diameter; hirsutulous.

Bud color: Nearest RHS 59D.

Flower: Perfect, campanulate, actinomorphic, about 7.0 mm long and 7.5 mm in diameter at face; flower attitude semi-downwards to outwards; individual flowers lasting about 4 days on plant or as cut flower and effective for two or three weeks as calyxes dark with age and persist; flowering beginning early summer without vernalization requirement and continuing until frost in Zeeland, Mich.

Calyx: Five, apex acute, hirsutulous; base fused in proximal half to form hypanthium; about 7.0 mm long and 2.0 mm wide.

Calyx color: Young flower abaxial color between RHS 64D and RHS 63C with lighter margin of less than 0.5 mm wide of lighter than RHS 65D in the distal two thirds, basal hypanthium portion nearest RHS 183C; young flower adaxial color nearest RHS 63D with narrow margin of less than 0.5 mm of lighters than RHS 62D; older flowers after petal abscission abaxial color nearest RHS 183C with 0.5 mm margin nearest RHS 187D and hypanthium base nearest RHS 178A; older flowers after petal abscission adaxial color nearest RHS 187D.

Petals: Five, glabrous, oblanceolate, acute apex and tapered base, entire, about 3.0 mm long and 1.0 mm wide in middle.

Petal color: Light pink, lighter and more pink than RHS N155D abaxial and adaxial young flowers, and developing nearest RHS 71C on abaxial and adaxial mature flowers.

Androecium:

*Filaments*.—Five, thin, glabrous; about 3.0 mm long and less than 0.5 mm diameter; fused to inner corolla; color white, lighter than RHS155D.

*Anthers*.—Basifixed with acute apex; glabrous; about 1.0 mm long and less than 0.5 mm diameter; color nearest RHS N163B.

*Pollen*.—Rare; color nearest RHS 18C.

Gynoecium: Two-beaked; bifid style with pistil split at ovary; 4.0 mm long.

*Ovary*.—Half-inferior; glabrous; about 2.5 mm long and 2.0 mm diameter, pointed apex ending in style, base rounded; color on distal portion nearest RHS 144C on young flowers and becoming tinted with RHS 187A on older flowers; color on basal portion of young flowers nearest RHS 183C; color on older flowers.

*Style*.—Two, glabrous; split apart at apex of ovary; about 6.0 mm long and less than 0.5 mm diameter; slightly curving splitting apart about 2.0 mm at distal region; color white, lighter than RHS 155D on young flower, and nearest RHS 187D with an apex white, lighter than RHS 155D on older flower.

*Stigma*.—Smaller than 0.5 mm diameter, globose; color lighter than RHS 145D.

Fruit: Two-beaked capsule, about 6 mm long and 3 mm in diameter at widest portion; color nearest RHS 199A when mature.

Seed: Ellipsoid; about 1.0 mm long and less than 0.5 mm wide; color nearest RHS 202A.

Disease and pest tolerance: The new plant grows best with ample moisture and drainage in either sun or shade. It is more tolerant of hot and humid environments than typical Coral Bell plants. Cold hardy from USDA zones 4 to 9. Other resistance and tolerance beyond that normal for *Heuchera* is not known.

I claim:

1. The new and distinct Coral Bells plant named *Heuchera* 'Berry Timeless' as herein described and illustrated with broad silver variegation between the dark-green regions surrounding the veins, flowering without vernalization requirement, from early summer to fall frost with coloring of light pink petals and effective, persistent, dark-rose calyxes just above foliage suitable for landscaping or as cut flower or foliage decoration.

* * * * *